United States Patent [19]

Carmichael

[11] Patent Number: 5,020,000
[45] Date of Patent: May 28, 1991

[54] MEASURING DRYNESS FRACTION

[75] Inventor: Richard Q. Carmichael, Huntley, United Kingdom

[73] Assignee: Spirax-Sarco Limited, Cheltenham, United Kingdom

[21] Appl. No.: 262,839

[22] Filed: Oct. 26, 1988

[30] Foreign Application Priority Data

Oct. 26, 1987 [GB] United Kingdom ................ 8725025

[51] Int. Cl.$^5$ .................. G01N 9/36; G06F 15/20
[52] U.S. Cl. ................... 364/500; 364/502; 73/29.01; 73/61 R
[58] Field of Search ........... 364/500, 502, 510, 558; 73/29, 61 R; 324/61 R; 374/42

[56] References Cited

U.S. PATENT DOCUMENTS

| | | | |
|---|---|---|---|
| 3,392,572 | 7/1968 | Brown | 73/29 |
| 3,430,483 | 3/1969 | Clawson et al. | 73/29 |
| 4,509,679 | 4/1985 | Longini | 374/42 |
| 4,576,036 | 3/1986 | Huang et al. | 73/29 |
| 4,679,947 | 7/1987 | Miller et al. | 73/29 |
| 4,836,032 | 6/1989 | Redus et al. | 73/29 |

FOREIGN PATENT DOCUMENTS

| | | | |
|---|---|---|---|
| 0001598 | 2/1963 | Japan | 374/42 |
| 0697288 | 9/1953 | United Kingdom | 374/42 |

Primary Examiner—Parshotam S. Lall
Assistant Examiner—Ellis B. Ramirez
Attorney, Agent, or Firm—Larson and Taylor

[57] ABSTRACT

This invention relates to the measurement of the dryness of steam supplied to steam-powered processes, and in particular to a method of making such measurements, and to methods of using the measured dryness fraction to obtain further information about the process plant and the steam supply.

In particular, the invention is applicable when fluid is supplied via a steam separator to a process, and it relies upon storing values for the efficiency of the separator at a plurality of input steam and condensate mass flow rates and a plurality of input fluid temperatures or pressures. Methods disclosed herein use one of these values, together with measured output steam and condensate mass flow rates, to calculate the dryness of the steam.

9 Claims, 3 Drawing Sheets

MEASURING DRYNESS FRACTION

This invention relates to the measurement of the dryness of steam supplied to steam-powered processes, and in particular to a method of making such measurements, and to methods of using the measured dryness fraction to obtain further information about the process plant and the steam supply.

In a conventional steam-powered process plant, saturated steam is supplied from a boiler to a number of individual processes via a steam main. Each process draws steam from the main via a separator, which removes the majority of the condensate, or wetness, from the steam, leaving it with a dryness fraction of typically 0.95 to 0.99. The majority of the heat is then removed from the steam in the process heat exchanger, causing it to condense, when it is returned to the boiler via the condensate return line.

Furthermore, it is known to provide a flow meter and a temperature or pressure sensor in the steam line between the separator and the process heat exchanger. The measurements from these instruments are fed to a flow/energy computer, which is then able to estimate the rate at which energy is supplied to the process.

However, if this rate of energy usage is to be measured accurately, it is also necessary to know the quality, or dryness, of the steam supplied to the process. Using conventional methods of determining the dryness fraction of a saturated steam flow, it is necessary to sample the flow, and either to calculate the necessary pressure reduction required to cause the sample to become superheated (throttling calorimetry), or to make simultaneous measurements of the density and temperature of the flow. The sample of fluid may not, however, be representative of the whole flow, and considerable inaccuracies can result.

Thus, the present invention seeks to provide a continuous, on-line method of calculating the dryness of the whole steam flow supplied to a process, such that the calculated value of the dryness may also be input to the flow/energy computer.

According to a first aspect of the present invention, there is provided a method of calculating the dryness fraction of fluid supplied via a steam separator to a process, the method comprising the steps of:

storing values for the efficiency of the separator (as herein defined) at a plurality of input steam and condensate mass flow rates and a plurality of input fluid temperatures or pressures;

measuring the mass flow rate, and the temperature or pressure, of fluid supplied to the process;

measuring the mass flow rate of condensate removed by the separator from the fluid;

relating the measured mass flow rates and the measured temperature or pressure to a corresponding stored value of the efficiency of the separator;

calculating the dryness fraction of fluid supplied to the process on the basis of said measured mass flow rates and the corresponding stored value of the efficiency of the separator.

Since there is a well known, fixed relationship between the temperature and the pressure of saturated steam, either parameter can be measured. However, temperature measurement is generally more accurate and less costly than pressure measurement; hence this method is preferred.

As used herein, the phrase "the efficiency of the separator" is defined as the percentage of the total liquid phase component of the input fluid which is removed by the separator. The efficiency will be a function of the pressure (and hence the temperature) of the input fluid, and of the steam and condensate mass flow rates.

According to a second aspect of the present invention, there is provided a method of calculating the rate at which energy is supplied to a steam-powered process, said process being supplied with steam via a separator, which removes at least a portion of the liquid content thereof, the method comprising the steps of:

measuring the mass flow rate, and the temperature or pressure, of fluid supplied to the process;

measuring the mass flow rate of liquid removed by the separator;

calculating the dryness fraction of fluid supplied to the process, using said measured flow rates and said measured temperature or pressure and a predetermined separation characteristic of the separator; and calculating said rate at which energy is supplied on the basis of said calculated dryness fraction.

According to a third aspect of the present invention, there is provided apparatus for calculating the dryness fraction of fluid supplied via a steam separator to a process, the apparatus comprising:

a first mass flow rate meter, for supplying a signal indicative of the rate at which fluid is supplied to the process;

a second mass flow rate meter, for supplying a signal indicative of the rate at which condensate is removed by the separator;

a temperature or pressure sensor, for supplying a signal indicative of the temperature or pressure of fluid supplied to the process; and a data processor, for receiving signals supplied by the first and second mass flow rate meters and the temperature or pressure sensor and for calculating the dryness fraction of fluid supplied to the process using a stored efficiency characteristic of the separator.

For a better understanding of the present invention, and to show how it may be brought into effect, reference will now be made, by way of example, to the accompanying drawings, in which.

Figure 1:
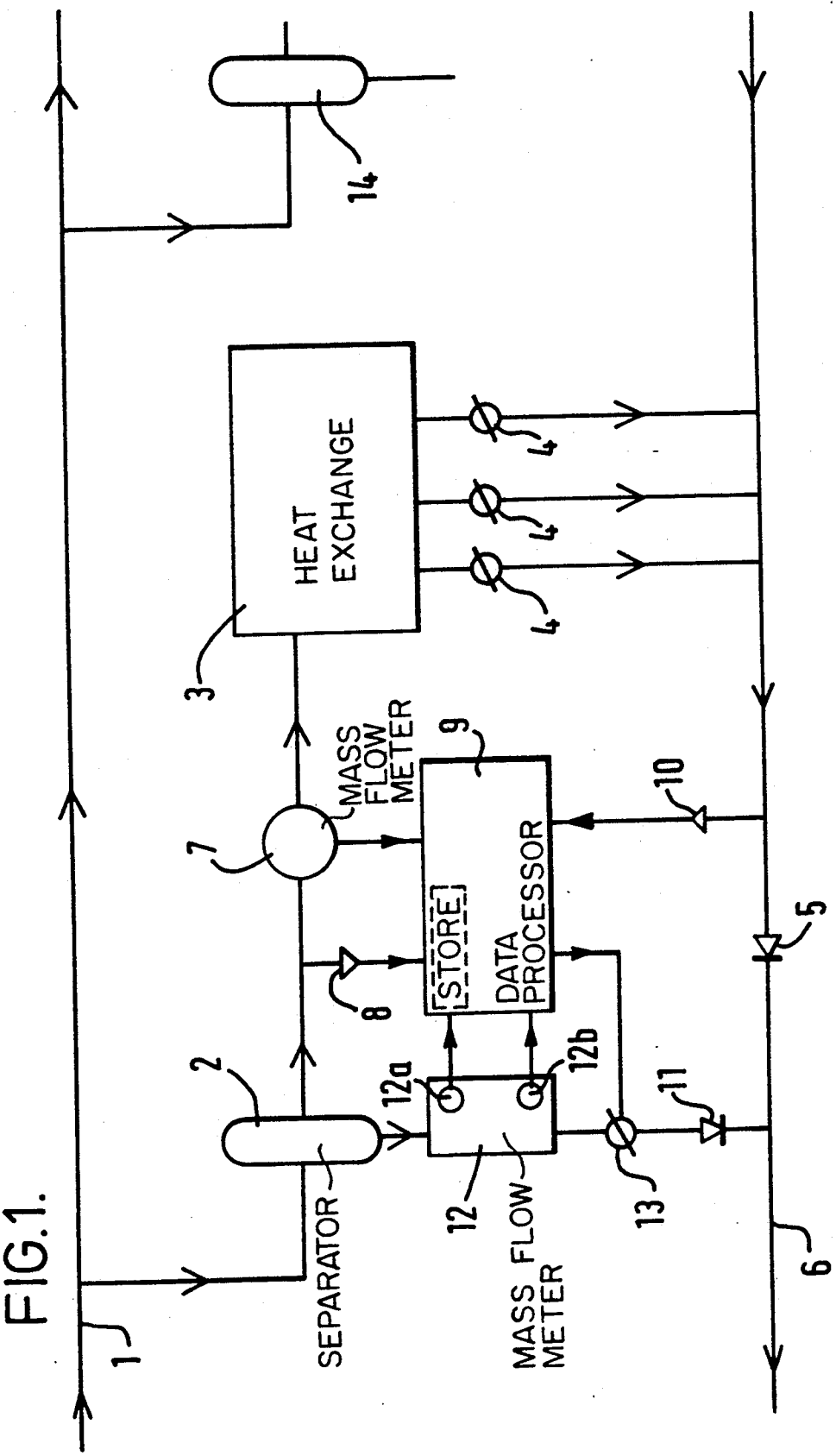
FIG. 1 is a block schematic diagram showing a steam-powered process plant, in which a method according to the present invention is used.

FIG. 1 shows a typical steam-powered process plant, in which saturated steam is supplied from a boiler to a number of individual processes via a steam main 1. The steam is passed via a separator 2 to a process heat exchanger 3. The majority of the condensate is removed from the saturated steam in the separator 2, and thus the steam supplied to the process heat exchanger 3 has a dryness fraction of typically 0.95 to 0.99. The majority of the heat is removed from the steam in the process heat exchanger 3, causing it to condense. The condensate is removed by steam traps 4, and returned through a non-return valve 5 to the boiler along the condensate return line 6.

A steam mass flow meter 7 and a temperature sensor 8 are located in the input steam line downstream of the separator, for sensing the temperature of steam supplied to the process heat exchanger 3, and the rate at which that steam is being supplied. Measurement signals from the mass flow meter 7 and the temperature sensor 8 are input to a data processor 9. A second temperature sensor 10 senses the temperature of condensate removed from the process heat exchanger 3 and returned to the boiler via the condensate return line 6. A temperature measurement signal from the second temperature sensor 10 is also input to the data processor 9.

The condensate removed from the input steam by the separator 2 is returned to the boiler via a second nonreturn valve 11 and the condensate return line 6. On leaving the separator 2, the condensate passes through a condensate mass flow meter 12 and a condensate trap 13. The condensate mass flow meter and trap may consist of two liquid level sensors 12a, 12b and a solenoid valve 13. These are connected to the data processor 9 as indicated in FIG. 1 in such a way that the time taken for the level of condensate to rise from the level of the lower level sensor to that of the upper level sensor is used as a measure of the mass flow rate of condensate. When the condensate level reaches that of the higher level sensor, the solenoid valve is opened, and the condensate is discharged through the non-return valve 11 until the level falls below that of the lower sensor.

It will be appreciated that the system illustrated in FIG. 1 is just one of a number of processes which would be supplied from a particular boiler, in practice, and a separator 14 supplying steam to a second process is also shown.

The present invention will now be illustrated with reference to FIG. 2 of the accompanying drawings. The calculations are carried out in the data processor 9, which may, for example, be the M200 flow computer, to which are passed measurement signals from the steam mass flow rate meter 7, the condensate mass flow rate meter 12, the steam temperature sensor 8, and the condensate temperature sensor 10.

However, before the necessary calculations can be carried out, it is necessary to store, in the data processor 9, details of the efficiency characteristics of the separator. The efficiency of the separator will depend upon the saturation temperature of the steam passing therethrough, and upon the mass flow rates of steam and condensate. Thus, before the invention may be put into practice, the separator, or, at least, the specific type of separator, which is to be used must be tested at a range of input steam temperatures and a range of condensate and steam mass flow rates, to allow the efficiency of the separator to be measured within those ranges. The efficiency characteristic is then stored in the data processor 9. The data processor 9 also stores specific enthalpy tables for both phases at all required saturation temperatures.

Figure 2:
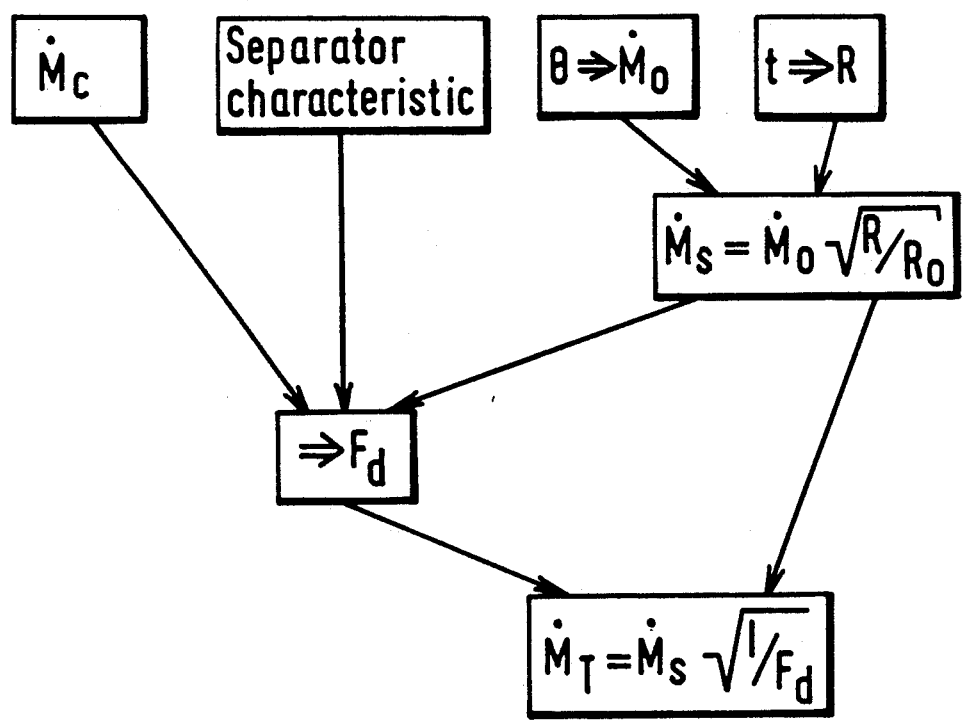
FIG. 2 is a flow diagram illustrating a method, according to a second aspect of the present invention, for calculating the rate at which energy is supplied to a steam-powered process.

The scheme illustrated in FIG. 2 shows the calculations which are necessary when using, as the steam mass flow rate meter 7, a meter incorporating a rotary variable differential transformer, such as that disclosed in U.K. Published Patent Application No. 8620931. In such a flow meter, a measure of the mass flow rate is derived from a flap angle $\theta$. The calibration of the device may be such that any given flap angle $\theta$ corresponds to a mass flow rate $\dot{m}_O$, which is the mass flow rate of 100% dry saturated steam at 8 bar which would produce that flap angle. Thus, the value of $\dot{m}_O$ measured must be compensated both for differences in pressure and in dryness of the steam flowing through the meter.

The temperature t of the steam sensed by the temperature sensor 8 corresponds to a vapour phase density R which may be read from look-up tables stored in the data processor. Then, if $R_O$ is defined as the vapour phase density at 8 bar, a mass flow rate $\dot{m}_S$ of 100% dry saturated steam at the operating pressure, indicated by the meter, is obtained from the relationship:

$$\dot{m}_S = \dot{m}_O \sqrt{R/R_O} .$$

Then, from the stored efficiency characteristic of the separator, and using the value of $\dot{m}_S$ calculated above and the mass flow rate $\dot{m}_C$ of condensate removed by the separator, it is possible to calculate the dryness fraction $F_d$ of the steam flow upstream of the separator and downstream of the separator, the latter of course being the dryness fraction of steam supplied to the process heat exchanger 3.

Then, once the dryness fraction of steam supplied to the process heat exchanger has been calculated, it is possible to compensate for the dryness of the flow to obtain a more accurate value for the mass flow rate of steam supplied to the process. In fact, the total mass flow $\dot{m}_T$ is related to $\dot{m}_S$ calculated above by the equation:

$$\dot{m}_T = \dot{m}_S \sqrt{1/F_d} .$$

Thus, by calculating the dryness fraction, as indicated above, it is possible to obtain a more accurate measurement of the total mass flow of fluid into the system than would otherwise be possible.

Alternatively, the steam mass flow meter 7 may be replaced by a differential pressure sensor, which measures the pressure drop across the separator. Associated with any restriction in a flow line is a characteristic number, the pressure discharge coefficient or Euler number EU. EU is defined as $$EU = \frac{\Delta p}{\frac{1}{2}RV^2}$$

($\Delta p$ = pressure drop
$R$ = fluid density
$V$ = flow velocity)

For certain sorts of separator (e.g. baffle type), EU is a constant, and thus measurements of $\Delta p$, using the differential pressure sensor, and of the fluid temperature (or pressure), and hence R from saturated steam tables, allow calculation of the steam flow velocity V (gas phase).

Since the effects of wet flow on $\Delta p$ will be negligible, the gas phase mass flow rate can be calculated in this way. As described previously, this flow rate, together with the measured condensate mass flow rate and the known efficiency characteristic of the steam separator, may be used to derive the dryness fraction of the steam supplied.

Once the total mass flow has been calculated accurately, and when the dryness fraction of the steam supplied to the process is known, the rate $P_{in}$ at which energy is supplied to the process may be calculated from the equation:

$$P_{in} = \dot{m}_T(h_{fg} F_d + h_{fa}),$$
where:

$h_{fg}$ = the specific heat of vaporisation at the saturation temperature; and $h_{fa}$ = specific enthalpy of the liquid phase at the saturation temperature.

In addition, it is possible to calculate the rate of energy wastage $P_{wa}$ due to condensate removal by the separator. Thus:

$$P_{wa} = \dot{m}_C (h_{fa} - h_{fb}),$$
where:

$h_{fb}$ = specific enthalpy of condensate at the boiler feed temperature.

In addition, since, in a closed system, the mass flow rate out of the process must be equal to the mass flow rate into the process, it is also possible to calculate the rate $P_{ret}$ at which energy is returned by the process:

$$P_{ret} = \dot{m}_T h_{fc},$$
where:

$h_{fc}$ = specific enthalpy of condensate at process removal temperature.

Thus, the rate $P_{wb}$ at which energy is wasted by returning condensate to the boiler is given by:

$$P_{wb} = \dot{m}_T (h_{fc} - h_{fb}).$$

Thus, it is possible to calculate the power consumption and efficiency of the process to a far higher degree of accuracy than has previously been possible.

If, in addition, the dryness of the steam output by the boiler is measured, it is possible to determine whether the condensate in the system arises from boiler carry-over, or from poor lagging, pipe work and plant design. Thus, the present invention also provides methods whereby inefficiencies, such as insufficient separation and trapping in the plant as a whole, will be revealed. Once the sources of the various inefficiencies have been located, it is possible to improve the efficiency of the plant as required.

Figure 3:
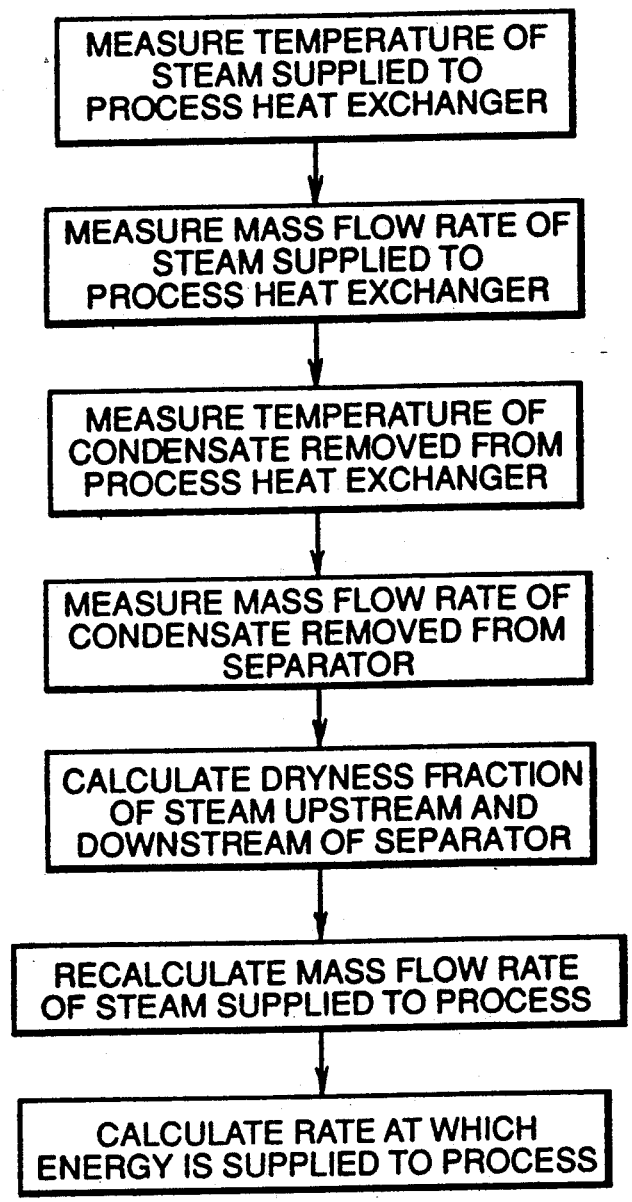
FIG. 3 is a flow chart setting forth the basic steps of a process according to one preferred embodiment of the invention.

Referring to FIG. 3, a flow chart is provided of the basic steps of an embodiment of the method of the invention wherein the temperature of the input fluid is measured. As illustrated, the basic method comprises four measuring steps which were described above, and three calculations which are made by microprocessor 9 and are based on the formulas set forth above.

I claim:

1. A method of calculating the dryness fraction of fluid supplied via a steam separator to a process, the method comprising the steps of:

storing values for the efficiency of the separator at a plurality of input steam and condensate mass flow rates and a plurality of values for the input fluid of a parameter from which the temperature of the input fluid can be derived;

measuring the mass flow rate, and the value of said parameter, of fluid supplied to the process;

measuring the mass flow rate of condensate removed by the separator from the fluid;

selecting a stored value of the efficiency of the separator corresponding to the measured mass flow rate and the measured value of said parameter;

calculating the dryness fraction of fluid supplied to the process on the basis of said measured mass flow rates and the corresponding stored value of the efficiency of the separator.

2. A method as claimed in claim 1, wherein said parameter is the temperature of the input fluid.

3. A method as claimed in claim 1, wherein said parameter from which the temperature can be derived is the pressure of the input fluid.

4. A method of calculating the rate at which energy is supplied to a steam-powered process, said process being supplied with steam via a separator, which removes at least a portion of the liquid content thereof, the method comprising the steps of:

measuring the mass flow rate, and the value of a parameter from which can be derived the temperature of fluid supplied to the process;

measuring the mass flow rate of liquid removed by the separator;

calculating the dryness fraction of fluid supplied to the process, using said measured flow rates and said measured value of said parameter and a predetermined separation characteristic of the separator; and calculating said rate at which energy is supplied on the basis of said calculated dryness fraction.

5. A method as claimed in claim 4, wherein said parameter is the temperature of the fluid.

6. A method as claimed in claim 4, wherein said parameter from which the temperature can be derived is the pressure of the fluid.

7. Apparatus for calculating the dryness fraction of fluid supplied via a steam separator to a process, the apparatus comprising:

a first mass flow rate meter for supplying a signal indicative of the rate at which fluid is supplied to the process;

a second mass flow rate meter for supplying a signal indicative of the rate at which condensate is removed by the separator;

a sensor for supplying a signal indicative of the value of a parameter from which can be derived the temperature of fluid supplied to the process; and a data processor for receiving signals supplied by the first and second mass flow rate meters and the sensor, for selecting a stored value of the efficiency of the separator corresponding the signals supplied by the first and second mass flow rate meters and the sensor, and for calculating the dryness fraction of fluid supplied to the process using the selected stored efficiency value of the separator, said data processor including a memory for storing values for the efficiency of the separator.

8. Apparatus as claimed in claim 7, wherein said parameter is the temperature of the fluid.

9. Apparatus as claimed in claim 7, wherein said parameter from which the temperature can be derived is the pressure of the fluid.

* * * * *